United States Patent [19]

Century

[11] Patent Number: 6,016,800
[45] Date of Patent: *Jan. 25, 2000

[54] INTRAPULMONARY AEROSOLIZER

[76] Inventor: Theodore J. Century, 702 W. Carpenter La., Philadelphia, Pa. 19119

[ * ] Notice: This patent is subject to a terminal disclaimer.

[21] Appl. No.: 08/957,125

[22] Filed: Oct. 24, 1997

[51] Int. Cl.$^7$ ................................................ A61M 11/00
[52] U.S. Cl. .......................... 128/200.22; 128/200.14
[58] Field of Search ................... 128/200.14, 200.22; 604/183; 600/5; 239/487, 488; 137/519.5, 533.11, 533.13, 533.15

[56] References Cited

U.S. PATENT DOCUMENTS

| | | | |
|---|---|---|---|
| 539,961 | 5/1895 | Russell | 239/488 |
| 1,223,243 | 4/1917 | Bessesen | 604/183 |
| 1,496,126 | 6/1924 | Livingstone . | |
| 1,796,455 | 3/1931 | Gunn et al. . | |
| 2,981,483 | 4/1961 | Pichon | 239/488 |
| 3,353,537 | 11/1967 | Knox et al. | 604/183 |
| 3,820,541 | 6/1974 | Langan . | |
| 3,903,886 | 9/1975 | Omotani | 604/193 |
| 4,122,836 | 10/1978 | Burnett . | |
| 4,471,765 | 9/1984 | Strauss et al. . | |
| 4,904,243 | 2/1990 | Bruera | 604/183 |
| 5,438,982 | 8/1995 | MacIntyre | 128/207.14 |
| 5,497,944 | 3/1996 | Weston et al. | 128/200.22 |
| 5,579,758 | 12/1996 | Century | 128/200.22 |

FOREIGN PATENT DOCUMENTS

| | | | |
|---|---|---|---|
| 45616 | 8/1910 | Austria | 239/488 |
| 1125042 | 10/1956 | France | 239/488 |
| 822065 | 10/1951 | Germany | 239/487 |
| 250211 | 9/1926 | Italy | 239/488 |
| 550429 | 10/1956 | Italy | 239/488 |
| 727236 | 4/1990 | U.S.S.R. | 239/487 |

OTHER PUBLICATIONS

Harvard Apparatus catalog, (Harvard Apparatus, Inc., South Natick, Mass.), Harvard Stainles Steel Syringes, p. A34.
Unimetrics brochure, (Unimetrics, Shorewood, Ill.), Gas & Liquid Sampling Syringes, pp. 14, 19 and back cover page.
Cole–Parmer 97–98 catalog, (Cole–Parmer Instrument Co.), Micromatic Syringe Pipettors, p. 195.
Medical Product Manufacturing News, Oct. 1997, Profile, p. 18.

*Primary Examiner*—Aaron J. Lewis
*Attorney, Agent, or Firm*—Paul & Paul

[57] ABSTRACT

An intrapulmonary aerosolizer comprises an aerosolizer attached to a pressure generator for delivery of liquid as an aerosol and which can be positioned in close proximity to the lungs by being inserted into the trachea directly or into an endotracheal tube or bronchoscope positioned within the trachea.

24 Claims, 13 Drawing Sheets

FIG. 5

INTRAPULMONARY AEROSOLIZER

BACKGROUND OF THE INVENTION

1. Field of the Invention

The present invention relates generally to the administration of drugs and drug therapy and more particularly to the introduction of drugs into the lungs.

2. Description of the Prior Art

Patients entering the hospital with pulmonary afflictions serious enough to require invasive treatment are generally subject to two types of procedure: 1) long-term ventilation, where the patient's breathing is augmented by air forced through an endotracheal tube inserted into the trachea, and 2) short-term (usually one day) treatment with a bronchoscope, a small fiber-optic device which is inserted directly into the trachea, enabling the physician to view specific areas of the upper respiratory tract, as well as individual bronchi and lobes of the lung. Patients requiring these treatments also generally require simultaneous administration of therapeutic substances directly to the lungs. In the case of the ventilated patient, drug administration is effected by the introduction of an aerosol of nebulized medicament into the ventilator air stream, a procedure with a notoriously variable, low efficiency (0–30%; typically 5–10%) of drug delivery in most hospital settings. In the case of the bronchoscopy procedure, substances can be administered in liquid form through the working channel of the bronchoscope, a small (1.2–2.2 mm diameter) opening, open at both ends, which traverses the length of the bronchoscope. For patients requiring pulmonary drug administration without either ventilation or visualization, a simple endotracheal tube is inserted into the trachea and the drug is delivered in liquid form, using an ordinary syringe.

Similar considerations apply to the administration of solutions of pulmonary test substances to experimental animals. Dosing with liquid to anesthetized subjects is either done directly, by inserting a small delivery tube into the trachea, or by first inserting a larger endotracheal tube, through which the liquid is then delivered. Delivery of significant amounts of inhaled aerosols to conscious experimental animals is even more problematic than aerosol delivery to anesthetized human subjects, owing to the fact that most small mammals are obligate nose breathers.

In general, then, while liquid delivery is fast, simple and inexpensive, distribution in the lung is uneven at best, with little alveolar involvement except if large volumes are administered, in which case the subject can suffer considerable respiratory distress. Further, the process can be a wasteful one, since much of the liquid bolus may be cleared, coughed up, and swallowed or expectorated. Nebulizer-generated aerosol delivery, on the other hand, while promoting a more uniform distribution of the delivered material in the lung, is slow, complicated and expensive. Because of the low and variable efficiency of delivery, dose quantification is difficult.

Recently, a promising alternative to these two modes of pulmonary drug delivery has emerged, termed "intratracheal aerosolization", which methodology involves the generation of a fine aerosol at the tip of a long, relatively thin tube which is suitable for insertion into the trachea, such as is illustrated in my prior U.S. Pat. Nos. 5,579,758; 5,594,987; and 5,606,789, which are each incorporated by reference herein. It is now well established that intratracheal aerosolization can be a highly effective alternative to liquid instillation and aerosol inhalation for the testing of pharmaceuticals in experimental animals. For example, radiograms of Technicium$^{99}$-labelled DNA-lipid complex administered to rats in this way have shown very deep and broad penetration into all lobes of the lungs. In another approach, intratracheal aerosolization of compounds which disrupt lung tissues (e.g., endotoxin, neutrophil elastase) has been shown to be 4½–5 times as effective as liquid instillation of these materials. In these and many similar applications, intratracheal aerosolization has proven to be a highly efficient, fast, and relatively inexpensive mode of pulmonary drug delivery. In addition, the effectiveness of this device in studies with experimental animals suggests its possible application to human subjects.

The present invention has been developed in view of the foregoing and discloses another pulmonary drug delivery device.

SUMMARY OF THE INVENTION

The present application discloses an intratracheal aerosolizer type of pulmonary drug delivery device and method of fabrication. As will be described in detail herein, one advantage of the present invention is that it can be applied to the fabrication of aerosolizers with the main body of the device being at least as small as 0.014" in diameter, and thus capable of being easily inserted into the working channel of a human bronchoscope (0.045"–0.087" diameter). Furthermore, this new device is capable of being flexed through angles and radii of curvature similar to those found at the flexible tip of a human bronchoscope, without exceeding the elastic limit of the aerosolizer or putting undue strain on the flexing mechanism of the bronchoscope.

In addition, this device can be inserted into adult and infant endotracheal tubes, and even into the very small, curved tubes (Murphy-style, 2.5 mm i.d., for example) which are used for nasal insertion in neonatal infants for the administration of surfactant in the treatment of infant respiratory distress syndrome.

Another advantage of the intratracheal aerosolizer of the present invention is that it can be positioned near the carina, or first bifurcation, and deliver a broadly-distributed and highly quantifiable dose of pulmonary medicament to the lungs of subjects including human subjects in the form of a fine, highly concentrated aerosol. In addition, the device in accordance with the present invention can be positioned so as to target a particular area of the lung, an individual bronchus, bronchiole, or lobe, f or example. For this reason, the applicant of the present invention has termed the present intratracheal aerosolizer an "intrapulmonary aerosolizer" and the process, "intrapulmonary aerosolization".

Another field of application of this new device relates to the delivery of therapeutic pulmonary test substances to mice; mice are much preferable to most other animals for early testing, due to their small absolute consumption of food and space, short gestational period, ease of genetic manipulation, and genomic similarities to humans. Other types of pulmonary drug delivery devices are too large or inflexible to be used routinely with mice in experimental studies, although well sized to be of use with rats and larger animals. The present device can be provided with a sufficiently small diameter, at least as small as 0.025" diameter, with main body tubes at least as small as 0.014" diameter, to be well suited for use with mice. Recent distributional studies in mice comparing the new sprayer with liquid instillation have shown the device to be effective and trouble-free in operation, reaching the deep lung with only a small fraction of the amount of material used for typical liquid instillation.

A further advantage of the intrapulmonary aerosolizer relates to the size of the particles which are produced by the device; for example, a preferred embodiment is described herein in which the device described operates at a pressure of about 2,000 psi and produces particles with a median mass diameter (MMD) of about 12 µm.

Unlike other relatively low-pressure aerosolizers, which require only a typical gas-tight syringe for liquid pressurization, the potential higher operating pressure of the newly-designed aerosolizer means that an ordinary gas-tight syringe will no longer suffice as the source of high-pressure fluid. An ordinary gas-tight syringe with luer-lock tip (e.g., Hamilton No. 81220), is rated for a maximum internal pressure of 500 psi. As a result, pressures much in excess of 700–750 psi will cause the glass barrel to crack, and the luer-lock tip to separate from the glass barrel. These considerations have led to the development of a new high-pressure syringe which is capable of withstanding internal pressures far in excess of the 2,000 psi operating pressures required for operation of the aerosolizer of the present invention.

In accordance with the present invention, an object is to provide a novel intratracheal aerosolizer.

It is another object of the present invention to provide a novel syringe capable of withstanding high internal pressures.

Another object of the present invention is to provide a sprayer device of sufficient size to permit insertion into the working channel of an animal or human bronchoscope, endotracheal tube or into the trachea directly.

It is another object of the present invention to provide a sprayer device which is thin and flexible enough to be used with a human bronchoscope, even a pediatric bronchoscope.

It is still another object of the present invention to provide a sprayer device small enough to be routinely applied to the dosing of mice with experimental substances as well as also being used with larger animals.

It is still another object of the present invention to provide an intratracheal sprayer device capable of generating an aerosol of particles sufficiently small in size for penetration deep into the lungs.

These and other objects of the present invention will become more readily apparent when taken into consideration with the following description and attached drawings.

BRIEF DESCRIPTION OF THE DRAWINGS

FIG. 5 is a front elevational view of an embodiment of an intrapulmonary aerosolizer in connection with an embodiment of a side arm reservoir.

DETAILED DESCRIPTION OF THE PREFERRED EMBODIMENTS

Figure 1:
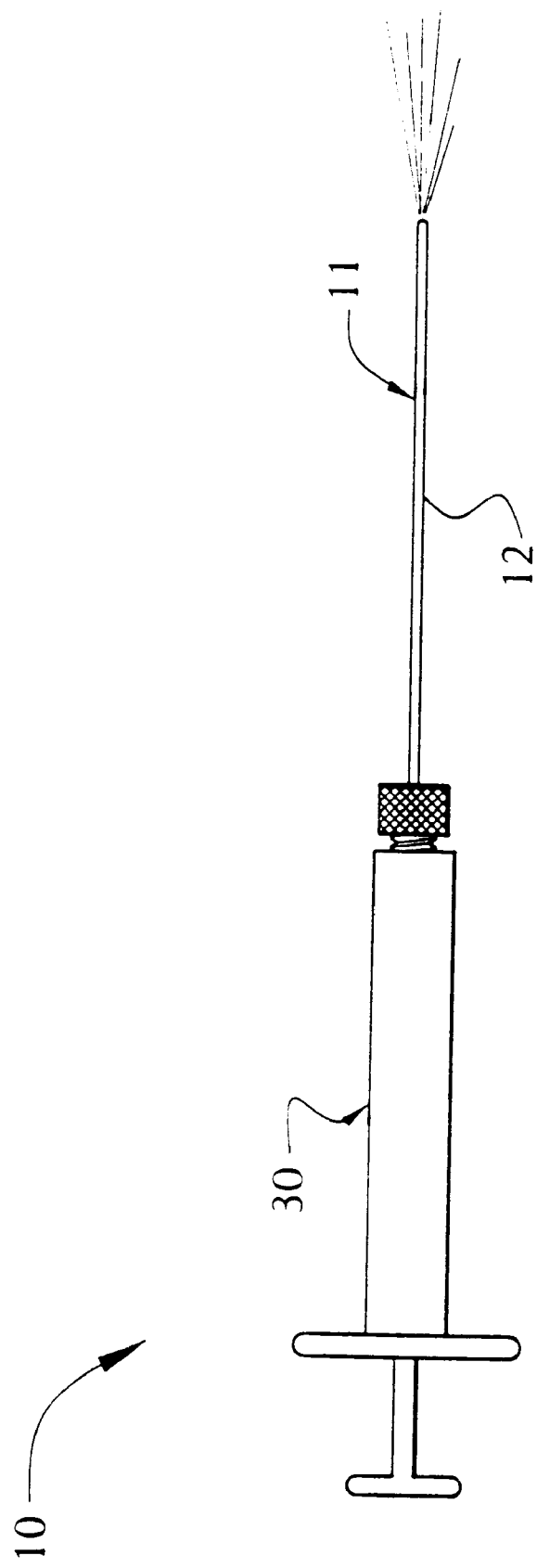
FIG. 1 is a front elevational view of an embodiment of an intrapulmonary aerosolizer in accordance with the present invention.

Referring now to the drawings in detail, wherein like reference numerals indicate like elements throughout the several views, there is shown in FIG. 1 a front elevational view of an embodiment of an intrapulmonary aerosolizer 10 in accordance with the present invention. The intrapulmonary aerosolizer 10 in accordance with the present embodiment comprises, as portions thereof, an aerosolizer 11 having a sleeve member 12, generally elongated and having a first end, a second end and a substantially longitudinally extending opening therethrough, with an aerosol generator disposed within the opening of the sleeve member 12, and a pressure generator 30 connected with the sleeve member 12, as will be described in more detail below.

Figure 2A:
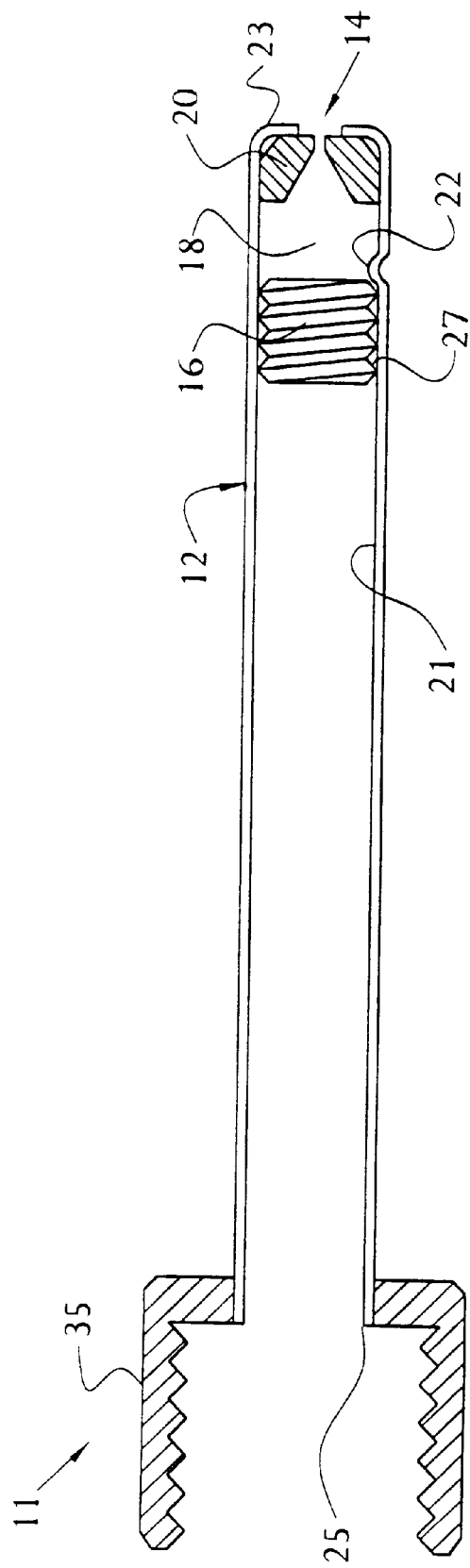
FIG. 2a is an enlarged, partially sectional front elevational view of an embodiment of an aerosolizer such as in FIG. 1.

A sectional front elevational view of the aerosolizer 11 is shown in FIG. 2a. The aerosol generator 14 in the present embodiment comprises as portions thereof an insert 16 comprising a swirl generator with at least one substantially helical channel or flute 27 on its external surface, a swirl chamber 18 and a body 20 comprising a final orifice, with these elements all being contained within the sleeve member 12, which is generally open at both ends. In addition, the aerosol generator 14 also preferably comprises insert captivation means and body captivation means for securing the insert 16 and body 20, respectively, within the sleeve member 12, which in the present embodiment is accomplished by a press-fit engagement between the insert 16 and body 20 with the inner wall 21 of the sleeve member 12. In the present embodiment, the body captivation means also comprises a first boss 23 extending from the inner wall 21 of the sleeve member 12, which preferably is comprised of a small lip 23 formed at the distal end of the sleeve member 12, which serves to retain the aerosol generating elements and more particularly the body 20 within the sleeve member 12. Further, in the present embodiment, the insert captivation means also comprises a second boss or dimple 22 in the inner wall 21 of the sleeve member 12, which, when the system is pressurized, serves to reinforce the generator elements in their proper spatial relationship through engagement of the second boss 22 with the insert 16. The distance between the helical insert 16 and the final orifice 20 defines the length of the swirl chamber 18. All of the internal components may be made from stainless steel, ceramics, or other suitable materials.

In operation, liquid is introduced into the proximal end 25 of the sleeve member 12, where the liquid encounters the helical insert 16, being then forced to follow the helical pathway defined by the helical channel 27 in the external wall of the insert 16 and the inner wall 21 of the sleeve member 12. When the liquid exits the helical channel 27, it enters the swirl chamber 18 and the direction of its flow is in a substantially circular pathway which follows the inner circumference of the sleeve member 12.

At the end of the swirl chamber 18, the rotating liquid encounters the final orifice 20, which forms an interface between the swirling liquid in the sleeve member 12 and the ambient atmosphere, usually air. Spray generation occurs at the final orifice 20 and preferably is characterized by the appearance of a space called the "air core" in the center of the emerging hollow cone of aerosol. The air core is contiguous with a small, pear-shaped space in the center of the swirl chamber 18, with the narrow, connecting "neck" of the air core located in the center of the final orifice 20.

The qualities of the spray (particle diameter and velocity, spray cone angle, etc.) are a complex function of many factors, including the incoming liquid pressure and rate of flow, the angle of approach of the rotating liquid as it enters the swirl chamber 18, the geometry (length and diameter) of the swirl chamber 18, the size and geometry of the final orifice 20, and ambient air conditions. In general, spray qualities are manipulated empirically, by observing how changes in the dimensions of individual elements affect the particular spray quality of interest.

In the present embodiment, the sleeve member 12 can comprise a piece of stainless steel tubing, preferably 0.025" outer diameter (o.d.)×0.0025" wall×0.020" inner diameter (i.d.) (23-gauge, extra thin wall), such as is available from Small Parts, Inc. of Miami Lakes, Fla. or MicroGroup Inc. of Medway, Mass., the length of which varies depending upon the application. For example, for most animal experimentation, the entire aerosolizer can be made of the sleeve member 12 so that the length will depend upon the subject, for example, 2" for rat, 3" for guinea pig, and the outer diameter of the aerosolizer will be 0.025" throughout.

Figure 2B:
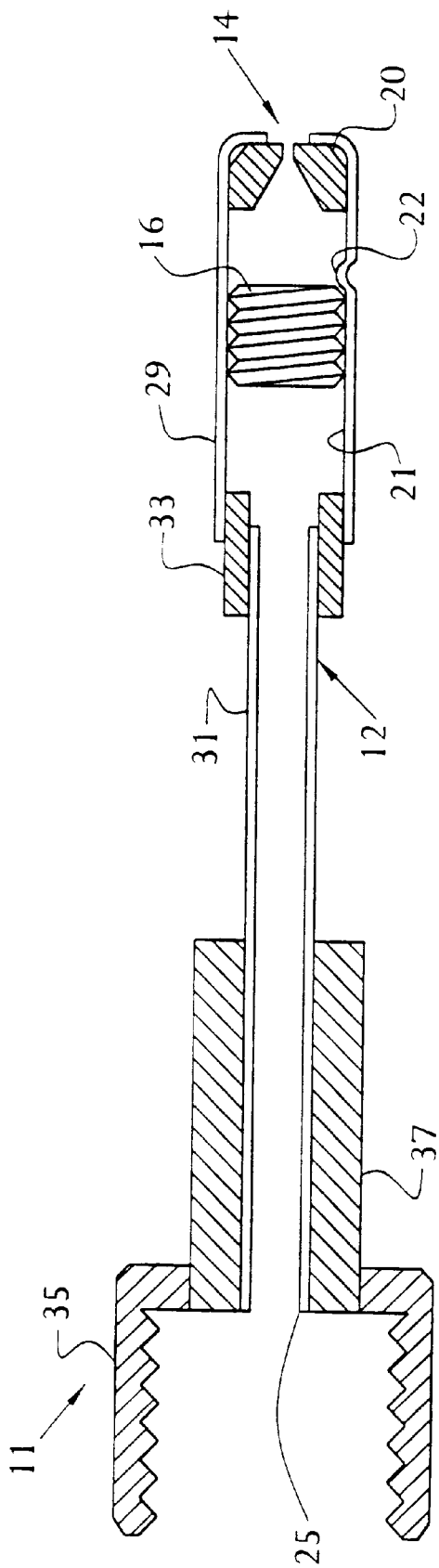
FIG. 2b is an enlarged, partially sectional front elevational view of another embodiment of an aerosolizer such as in FIG. 1.

Illustrated in FIG. 2b is a sectional front elevational view of another embodiment of the aerosolizer 11 of FIG. 1. As will be described in detail herein, one advantage of the aerosolizer 11 shown in FIG. 2b is in its application to large animals and human subjects, where a bronchoscope may be employed. As illustrated in FIGS. 2a and 2b, the sleeve member 12 preferably comprises a short length of tubing 29 (preferably ⅛"–¼") of 0.025" o.d. tubing, which is attached, preferably by brazing or welding, to a longer length of tubing 31, preferably an 18"–28" piece of stainless steel tubing, which is only 0.014" o.d., thus giving the aerosolizer much greater flexibility. Further, to better accommodate the transition between the two sizes of tubing 29 and 31, a short length of intermediate-sized tubing 33 may also be used between the two tubes 29 and 31, or the larger tubing 29 can be swaged down from an inner diameter of 0.020" to 0.014", thus engaging the outer diameter of the smaller tubing in a sliding press fit so as to facilitate the brazing or welding process.

Figure 2C:
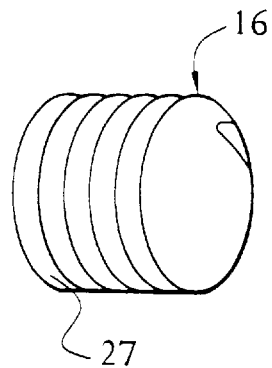
FIG. 2c is an isolated perspective view of an insert in accordance with the intrapulmonary aerosolizer of FIG. 1.

To place the aerosol-generating elements inside the sleeve member 12 as shown in FIGS. 2a and 2b, the sleeve member 12 is preferably retained in a given position, such as by a fixture, so as to be aligned axially with a sub-miniature quantitative arbor press comprised, for example, of a small micrometer head with appropriately sized ram tooling, although other methods can also be used. In accordance with the preferred method for installing the aerosol-generating elements, the ram of the arbor press (preferably 0.018" diameter) slides inside the 0.020" i.d. of the sleeve member 12, which permits the precise placement of the generator elements, which are 0.020" in outer diameter in the present embodiment. The helical insert 16 is introduced into one end of the sleeve member 12. In the present embodiment, as best illustrated in the isolated perspective view of FIG. 2c, the helical insert 16 is comprised of a small length (preferably 0.030"–0.040") of rod, preferably of stainless steel and 0.020" in diameter, the outside of which contains the at least one helical channel 27, preferably 0.006" wide×0.005" deep, similar in appearance to a small screw. For example, in the present embodiment, the insert 16 can be comprised of a 0000-160 machine screw, such as is available from J.I. Morris Co., Southbridge, Mass., which is ground flat and deburred after the head is removed. The ram of the arbor press is then advanced until it contacts the helical insert 16 and pushes it into the sleeve member 12, which in this embodiment is for a distance of about 0.040" from the end of the sleeve member 12. The outer diameter of the helical insert 16, 0.020" in the present embodiment, matches the inner diameter of the 0.025" o.d. tube (wall thickness= 0.0025"), so that there is a sliding press fit between the two elements, and any pressurized liquid introduced into the tube is constrained to follow the pathway defined by the helical channel 27 of insert 16 and the inner wall 21 of the sleeve member 12, and cannot simply move parallel to the longitudinal axis of the sleeve member 12.

Figure 2D:
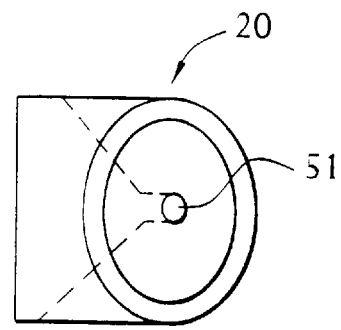
FIG. 2d is an isolated perspective view of a body in accordance with the intrapulmonary aerosolizer of FIG. 1.

In the present embodiment, the body 20 as illustrated in the isolated perspective view of FIG. 2d defines a first end, a second end and an opening 51 therethrough, and which preferably is comprised of a conventionally available sapphire or stainless steel orifice, such as is available from Bird Precision of Waltham, Mass., preferably 0.020" in diameter, with 0.0026" inner diameter, which is similarly inserted into the sleeve member 12, leaving space for the swirl chamber 18. The body 20 may also be comprised of other suitable components and of other suitable materials. The orifice 20 is pushed inside the end of the sleeve member 12 so that the lip 23, preferably approx. 0.010" in length in this embodiment, extends beyond the end of the orifice 20. The lip 23 is then formed over the edge of the orifice 20, preferably using a conventionally available small forming die, although other suitable methods may also be employed. The orifice 20 and the other elements are thus secured in their proper spatial arrangement inside the sleeve member 12, but there is enough open area in the center to allow the escape of aerosol emanating from the opening in the center of the orifice 20.

In addition, the strength of the lip 23, which is critical for retaining the aerosolizer elements within the sleeve member 12 when high pressures are applied, may be significantly reinforced beyond the strength of the base metal (stainless steel alloy 304 or 316) by the application of a small bead or layer of nickel-chromium brazing alloy (AMS 4777), such as Nicrobraz LM from Wall Colmonoy Corp., Madison Heights, Mich., or Ni-Flex 77 from Materials Development Corp., Medford, Mass. The hardness of these materials exceeds that of the base metal by a factor of 5 (Rockwell "C" scale 60 compared to 12), although their melting points are low (1800° F.) compared with the melting point of stainless steel (2600° F.) or sapphire (3100° F.). These properties make these materials ideal for use in this application.

Finally, in the present embodiment, the second boss or dimple 22 may be formed in the wall 21 of the sleeve member 12 between the orifice 20 and the helical insert 16, which is accomplished in the present embodiment by using a pair of modified pliers; however, other devices may also be employed for this purpose. The dimple 22 prevents the insert 16 from moving up against the orifice 20 when the system is pressurized. The distance between the orifice 20 and the insert 16 defines the length of the swirl chamber 18, and any shortening of this distance will impair the performance of the aerosolizer.

Figure 2E:
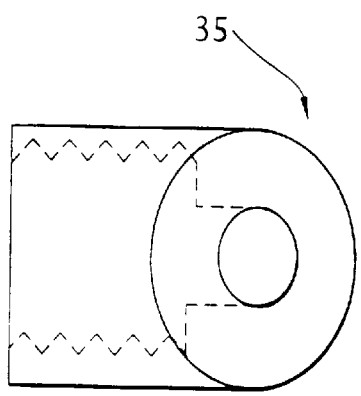
FIG. 2e is an isolated perspective view of a coupling means in accordance with the intrapulmonary aerosolizer of FIG. 1.

As illustrated in FIGS. 2a and 2b, when the sprayer tip is complete, coupling means 35 is preferably attached to the proximal end 25 of the sleeve 12, which in the present embodiment preferably comprises a special stainless steel flat-bottom fitting with ¼"–28 internal threads, as illustrated in the isolated perspective view of FIG. 2e, and which is attached, such as by brazing, to the proximal end 25 of the sleeve member 12. The fitting 35 provides a high-pressure, leak-tight connection for the sleeve member 12. Further, as shown in FIG. 2, a short length of heavy-walled tubing 37 may also be used to provide a transition from the smaller diameter tube 31 of the sleeve member 12 to the fitting 35, in order to provide strain relief.

Figure 3:
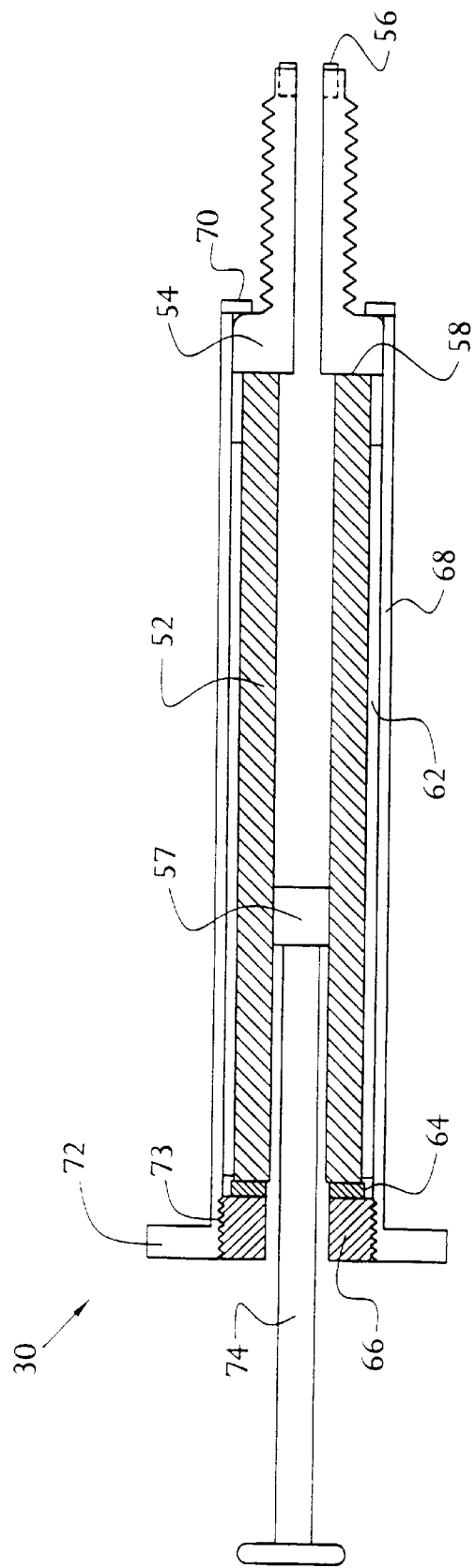
FIG. 3 is an enlarged partially sectional front elevational view of an embodiment of a pressure generator such as in FIG. 1.
Figure 4:
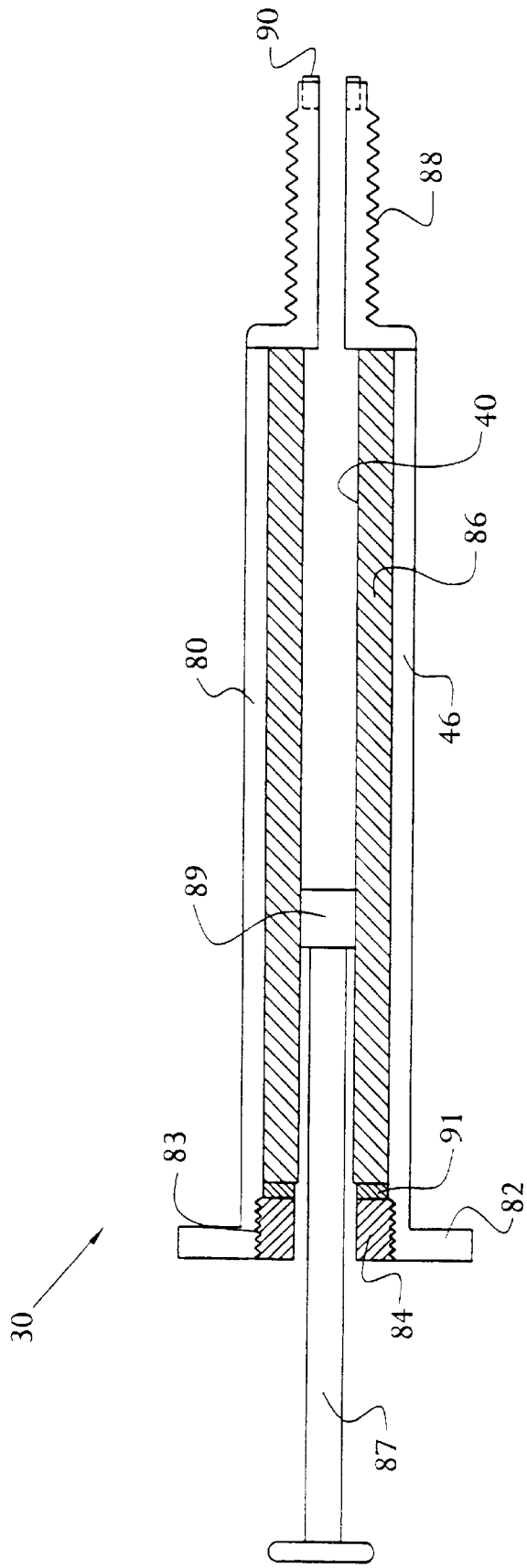
FIG. 4 is an enlarged, partially sectional front elevational view of another embodiment of a pressure generator of FIG. 1.

In order for the aerosol generator 14 to produce a sufficiently fine aerosol, the aerosol generator 14 preferably is provided with a source of high-pressure liquid via a pressure generator 30. In particular, the aerosol generator 14 described preferably receives liquid pressurized to about 2,000 psi. In the present embodiment, the pressure generator 30 preferably comprises a high-pressure syringe as illustrated in FIGS. 3 and 4 being of a type where a seal affixed to a piston seals against a polished internal surface of a cylinder, although other configurations may work as well, e.g., those where a seal located within the bore of the cylinder seals against the polished external surface of a piston. In addition, many other ways of providing high-pressure liquid to the aerosol generator 11 can also be used, such as a small high-pressure reciprocating pump (e.g., chromatography pump), or other suitable types of syringes, for example.

In the present embodiment described herein, the syringe 30 preferably has a capacity of 250 microliters ($\mu$l) (0.25 ml). Once this amount has been delivered, the syringe 30 must be disconnected from the aerosolizer 11, refilled with liquid, and reconnected to the aerosolizer 11 before delivering another 250 $\mu$l dose. As will be described herein, the present invention also discloses a valving system which can be interposed between the syringe 30 and the aerosolizer 11, which allows the syringe 30 to be re-filled from a reservoir without having to disconnect the syringe 30 from the aerosolizer 11.

A high-pressure syringe in accordance with a preferred embodiment of the present invention comprises an inner body member, preferably a glass cylinder, and a piston or plunger preferably of stainless steel. Further, preferably a high-pressure seal between the piston and the cylinder is effected with a plug, such as of Teflon, which is attached, such as by being swaged, onto the tip of the stainless steel piston. In the preferred embodiment of the high-pressure syringe, the glass cylinder would crack in operation when the internal pressure would exceed about 700 psi. In view of which, in accordance with the present embodiment, the entire glass cylinder is encased in an outer body member, preferably comprising a stainless steel housing; stainless steel has a tensile strength which exceeds that of glass by a factor of about 22. An advantage of the design of the present embodiment is that the cylinder will not fail; for example, at extremely high-pressures (such as 5,000–8,000 psi) the Teflon plug will fail first. In view of which, the high-pressure syringe in accordance with the present embodiment can be used to routinely pressurize liquids to any desired pressure, which in the present embodiment is to preferably about 2,000 psi to energize the aerosolizer 11 described above. In other embodiments, the plug referred to above may be comprised of an "O"-ring seal, such as Viton, and the inner body member may be comprised of metal, preferably stainless steel or suitable plastic, such as PEEK. In this case, the outer body member may be eliminated.

The limited capacity of the syringe in the presently preferred embodiment (250 $\mu$l) relates directly to the small area of the piston tip (approx. 4.2 mm$^2$; diameter=2.3 mm). The magnitude of the piston tip area determines the force required to generate a given pressure inside the cylinder; in the present design, the piston area is such that a normal person can easily offer the amount of thumb pressure required to generate 2,000 psi pressure in the syringe.

As best illustrated in FIG. 3, a high-pressure syringe in accordance with the present embodiment may be made from a standard 250 $\mu$l gas-tight syringe comprising an inner body member 52 defining a glass barrel and threaded stainless steel nose 54 with a Kel-F tip seal 56, such as is available from Hamilton of Reno, Nevada or Unimetrics Corp. of Shorewood, Ill. When the standard syringe is constructed, the stainless steel nose 54 is sealed onto the glass barrel 52 at the distal end 58 of the syringe, such as with epoxy. Generally, as discussed earlier, this arrangement works well as long as the pressure inside the syringe does not exceed about 700 psi. At higher pressures, encasing the barrel of the syringe in an outer body member comprised of stainless steel prevents axial cracking, as set forth in detail above. However, support is also required to be give n to the syringe nose 54, or else the barrel 52 may crack circumferentially where it joins the nose 54, or the nose 54 may separate from the barrel 52. For this reason, construction of the high-pressure syringe utilizing a standard gas-tight syringe involves axial support for the ends of the syringe as well as circumferential protection for the glass barrel 52, as will be described below.

Figure 3A:
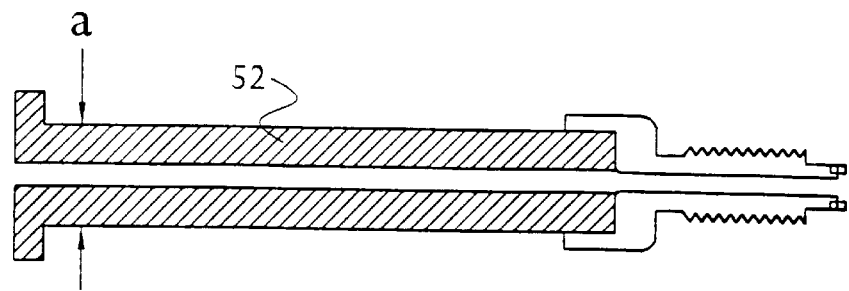
FIGS. 3a–3c are partially sectional front elevational views illustrating assembly of the pressure generator of FIG. 3.
Figure 3B:
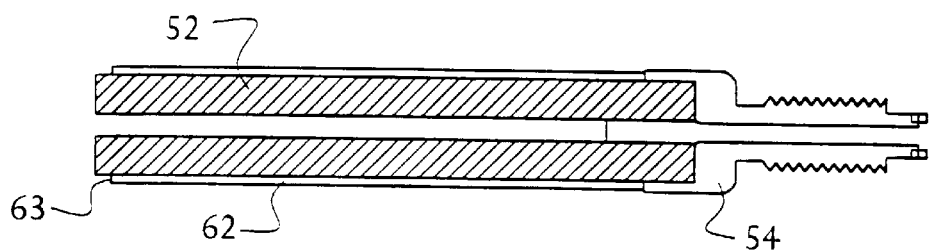
Figure 3C:
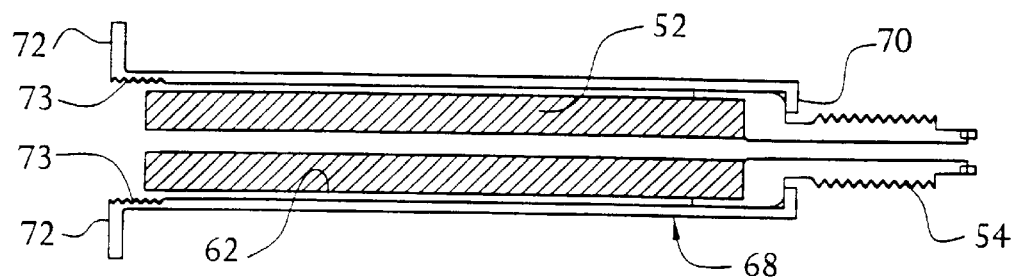

Construction of the high-pressure syringe utilizing a standard syringe is illustrate d in FIGS. 3a–3c. As shown in FIG. 3a, the glass barrel 52 of the standard syringe is slightly shortened at its proximal end shown at arrows "a" by removing that part of the barrel 52 which includes the two glass flanges (preferably, about the first ³⁄₁₆"–¼"), which is the portion that prevents the syringe from slipping between the fingers when the plunger is depressed with the thumb when the syringe is ordinarily used. Also, this part of the barrel 52 is usually slightly larger in diameter than the rest of the barrel, so that once this part is removed, the barrel 52 is straight, with a plain end, and uniform outer diameter, usually 0.303"–0.305". As shown in FIG. 3b, a first stainless steel tube 62 comprising a first outer body member, preferably ⅜" o.d. with 0.034" wall, such as is available from McMaster-Carr Supply Co. of New Brunswick, N.J. or MicroGroup, Inc. of Medway Mass., is then slid over the glass barrel 52 until it abuts the shoulder of the stainless steel threaded nose 54 at the point where it joins the glass barrel 52. Before assembly, preferably both the outer surface of the glass barrel 52 and the inner surface of the first tube 62 are coated with a thin film of epoxy. When cured, the epoxy coating provides support for the glass barrel 52 by filling any small voids which might exist between the barrel 52 and the first stainless steel tube 62.

The length of the first stainless steel tube 62 is such that, once in place, the end of the glass barrel 52 protrudes from the proximal end 63 of the first tube 62, preferably by some 0.020". This protrusion provides a sealing surface against which a gasket 64 impinges, driven by a retaining member 66, which is described in detail below.

As illustrated in FIG. 3c, in preparation for the final assembly, a second stainless steel tube 68 comprising a second outer body member, preferably 7/16" diameter with a 0.031" wall, is modified in three ways: 1) the distal end is fitted with a stainless steel washer 70 preferably 7/16" o.d., 1/4" i.d., 1/16" thick, which is attached, such as by brazing or welding, to the end of the second tube 68; 2) the proximal end is fitted with two flanges 72, preferably of stainless steel which are similar to the ones removed from the glass syringe, to lend finger support when the plunger is depressed with the thumb; and 3) the inner diameter of the second tube 68 is preferably threaded over a length of about 1/8" from the end with a fine (preferably 10 mm×0.5 mm) thread 73.

The syringe barrel 52, with its attached protective stainless steel tube 62, is then slid into the modified second tube 68, the mating surfaces having preferably been coated with epoxy prior to assembly. The washer 70 at the distal end of the second tube 68 permits the 1/4"–28 threaded nose 54 of the syringe to pass through, but acts as a stop when the larger diameter of the syringe nose shoulder is encountered. At this point, preferably about 1/8" of the proximal end of the second tube 68, the portion with the internal thread 73, extends beyond the proximal end of the glass barrel 52, which protrudes slightly beyond the end of the first tube 62. As shown in FIG. 3, a small washer-shaped gasket 64, preferably a polyimide gasket, approx. 0.020" thick, is then placed inside the second tube 68 against the end of the glass barrel 52 and the retaining screw 66 is run home with a 1/8" hex wrench, completing the jacketing of the glass syringe, which is then completely supported on all surfaces and cannot move, either axially or circumferentially, when high internal pressures are applied. In the present embodiment, the retaining member 66 comprises a screw preferably approx. 0.075" long, with a 10 mm×0.5 mm external thread, which is fashioned out of stainless steel. This retaining screw 66 in the presently preferred embodiment has a hexagonal hole through the center which measures 1/8" across the flats, although other shaped holes may also be utilized. This hole serves two functions: 1) to provide a means whereby the screw 66 can be driven home, and 2) to provide a hole with sufficient clearance to allow the syringe plunger 74 having the plug 57 to pass in and out of the syringe barrel 52. Although not shown, the syringe plunger 74 may include graduations or other markings in order to measure the amount of liquid contained in the syringe 30.

As illustrated in FIG. 4, a high-pressure syringe in accordance with the present embodiment may also be constructed from component parts. A difference is that only a single outer body member 80 comprised preferably of tubular stainless steel is used, with an outer diameter in this embodiment of preferably 7/16", similar to that described above for the second tube 68 of the previous high-pressure syringe, but with a wall thickness of 0.065". This single tube 80 is also similar to the second tube 68 of the previous design in that the proximal end also features flanges 82 for finger support and a small length of fine internal thread 83 at the mouth of the tube (preferably 8.5 mm×0.5 mm). A similar retaining screw 84 is used for the final enclosure of the inner body member 86, also preferably of glass.

The threaded nose 88 of the present syringe is preferably fashioned from stainless steel and attached, such as by being brazed or welded, onto the end of the tube 80, forming the distal end of the high-pressure syringe. A high-pressure seal 90, such as a polyimide, PEEK or fluoropolymer seal is preferably pressed into a counterbore in the end of the threaded nose 88, with sufficient seal material protruding from the tip (preferably 0.010"–0.015") to effect a high pressure seal when the syringe and aerosolizer are screwed together and made finger-tight.

The inner body member 86 comprises an appropriate length of glass tubing, preferably precision-bore 0.0907"-diameter glass capillary tubing (e.g. Ace Glass Co., Inc., Vineland, N.J.) and is inserted into the stainless steel tube 80 after the mating surfaces preferably have been coated with epoxy. A small sealing gasket 91 is preferably placed on the end of the glass tube 86, and the threaded retaining screw 84 is run home with a 1/8" hex wrench. A plunger 87, preferably of stainless steel and having a plug 89 similar to the plunger 74 with plug 57 is also provided to operate the device, such as is available from Hamilton of Reno, Nev.

As described earlier, the protocol for use of the aerosolizer/syringe system depends upon the application. For example, when applied to the dosing of experimental animals, especially small mammals, the aerosolizer 11 may be housed within a sleeve member 12 that is short (2" length for rats, 3" for guinea pigs, etc.) and relatively stiff, such as being made of a single length of 0.025" o.d. tubing (23-gauge), as shown in FIG. 1. In order to operate the aerosolizer/syringe device, preferably the sleeve member 12 containing the aerosolizer 11 is detachable from the syringe, which in the presently preferred embodiment is by unscrewing the two parts from each other, at which point the syringe is loaded with liquid, such as experimental solution, and the aerosolizer and syringe are re-attached. The sleeve member 12 containing the aerosolizer 11 is then inserted into the subject's trachea, by being inserted through the mouth or nose and either with or without an endotracheal tube, and, when the tip of the aerosolizer is preferably near (but not touching) the first bifurcation (the carina), the syringe plunger is firmly depressed. The aerosolizer and endotracheal tube can then be removed.

For larger animals and human subjects, where very deep lung penetration or specific localization of the sprayed material is desired, a bronchoscope may be used to visualize the area to be targeted. In this case, the aerosolizer 11 may be constructed so as to include a length of thin, highly flexible material, preferably 28-gauge tubing (0.014" o.d.) in a preferred embodiment, and only the very tip, which houses the generator 14 within the sleeve member 12, is constructed of 23-gauge tubing, as illustrated in FIG. 2. The aerosolizer constructed in this way is suitable for insertion into the working channel of even the smallest bronchoscope (0.045" diameter), and is flexible enough to withstand the bronchoscope tip deflection through most of its range, without either exceeding the elastic limit of the aerosolizer tube or taxing the tip deflection mechanism of the bronchoscope.

When the present invention is used in conjunction with a bronchoscope, preferably the bronchoscope is first inserted into the subject's trachea and located in the specific area to be targeted. The aerosolizer 11 is then inserted into the working channel of the bronchoscope until the tip of the aerosolizer protrudes preferably about 3–5 mm beyond the end of the bronchoscope. Alternatively, the system can be previously measured and calibrated so that when the shank of the aerosolizer is fixed in place at the entrance to the working channel (e.g., with a luer-lock fitting with a set screw), the distal tip protrudes the requisite amount. Next, the syringe is filled by placing the tip in the solution to be sprayed and pulling back on the plunger. The tip of the syringe is then threaded into the high-pressure connector of the fitting 35 on the end of the aerosolizer and made finger-tight, thus effecting a high-pressure seal between the seal 56 in FIG. 3 (90 in FIG. 4) in the tip of the syringe and the flat bottom of the fitting 35 on the aerosolizer. To deliver the dose, the operator simply pushes firmly on the syringe plunger.

To re-dose the subject with another volume of 250 µl, the syringe must be detached (unscrewed), refilled, reattached, and the plunger again depressed. For larger dosages, such as 1 ml (four filling/delivery cycles), the bronchoscope and aerosolizer are left in place, and the syringe is cycled for each 250 µl dose. However, when dosages approach 3 ml, this process becomes less desirable, in part because of the greatly increased opportunity for organic and inorganic contamination to enter the system.

Figure 5:
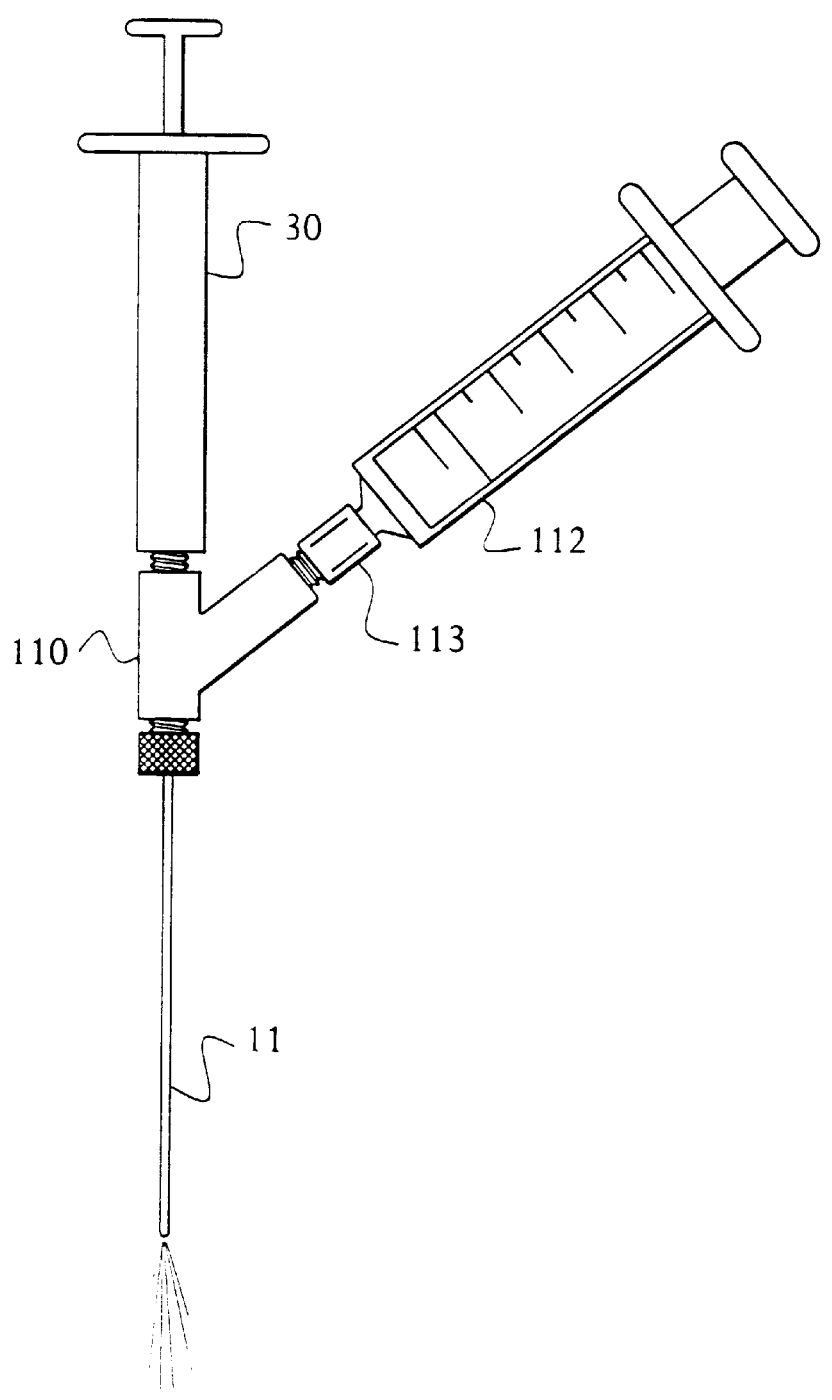

The administration of multiple 250 µl doses can be simplified by the interposition of a side-arm reservoir. Briefly, as shown in FIG. 5, the high-pressure syringe 30 is attached to the entry port of one embodiment of a sidearm adapter 110, the exit port of which is attached to the connector end of the aerosolizer 11. More specifically, between the high-pressure syringe and the aerosolizer 11 is the sidearm adapter 110, which accesses a reservoir 112, such as a 5-ml glass syringe in the present embodiment, which attaches to the sidearm by way of a fitting 113, available, for example, from S4J Manufacturing Services, Inc. of New Brunswick, N.J. Further, as best illustrated in the fragmentary enlarged sectional view of the sidearm adapter 110 of FIG. 6, between the reservoir 112 and the main port 131 of the sidearm adapter 110 is preferably a check valve 114, which in this embodiment consists of a ruby ball 116 that impinges on a sapphire seat 118 when the system is pressurized, although other types of high-pressure valving systems (push-pull, rotary, etc.) may work as well. Taken together, this system constitutes a small manual reciprocal pump, or mini-pump, as described below.

Figure 6:
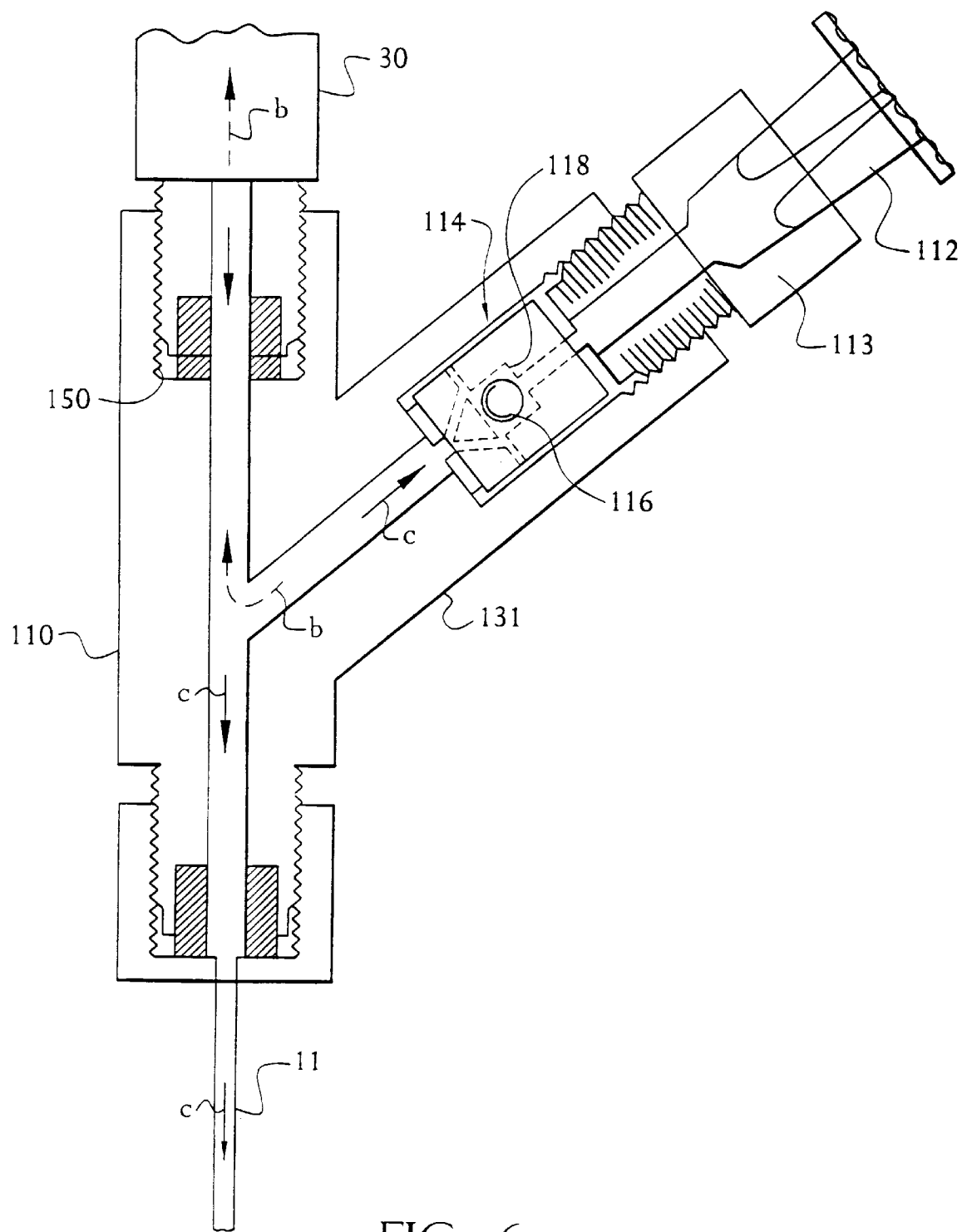
FIG. 6 is a fragmentary enlarged, partially sectional view of the side arm reservoir of FIG. 5.

While the separate pump elements comprising the high-pressure syringe 30 and the side-arm adapter 110 shown in FIGS. 5 and 6 may be independent and reversibly connected to one another via the threaded syringe tip 54 and 88 shown in FIGS. 3 and 4 respectively, and the threaded female port 150 on the adapter 110, these two elements may also be constructed as a single unit, eliminating the threaded elements 54 and 88 in both cases and attaching, such as by brazing or welding, the stainless steel tube 80 of FIG. 4 and the stainless steel tube 68 or washer 70 of FIG. 3 directly to the sidearm adapter 110 of FIG. 5. The two parts thus combined will appear similar to the way they do in FIGS. 5 and 6, except that the threaded elements have been replaced by a brazed or welded joint. For applications where the intrapulmonary aerosolizer is to be used mainly for multiple dosing, this combining of the two pump elements into a single unit greatly simplifies the construction of this device.

At near-ambient pressures, the tiny opening in the orifice 20 in the tip of the aerosolizer 11, as shown in detail in FIGS. 2*a* and 2*b*, is essentially closed compared with the smallest passage through the reservoir syringe 112/side arm adapter 110 combination, the orifice 20 being smaller than the syringe 112/adapter 110 passages by a factor of about 600. For this reason, pulling back on the plunger of the high-pressure syringe 30 results in liquid flowing in the direction of arrow "b" from the reservoir 112 into the high-pressure syringe 30. When the high-pressure syringe 30 is full, depressing the plunger firmly will result in liquid flowing in the direction of arrow "c" which forces the ball 116 against the seat 118, closing the check valve 114 and allowing pressure to build in the system, resulting in the generation of a fine aerosol at the tip of the aerosolizer 11. By working the plunger of the high-pressure syringe 30 in a reciprocal motion, this process can be repeated until the reservoir 112 is emptied. In this way, several milliliters of material can be delivered without detaching the high-pressure syringe 30 from the system.

Figure 7:
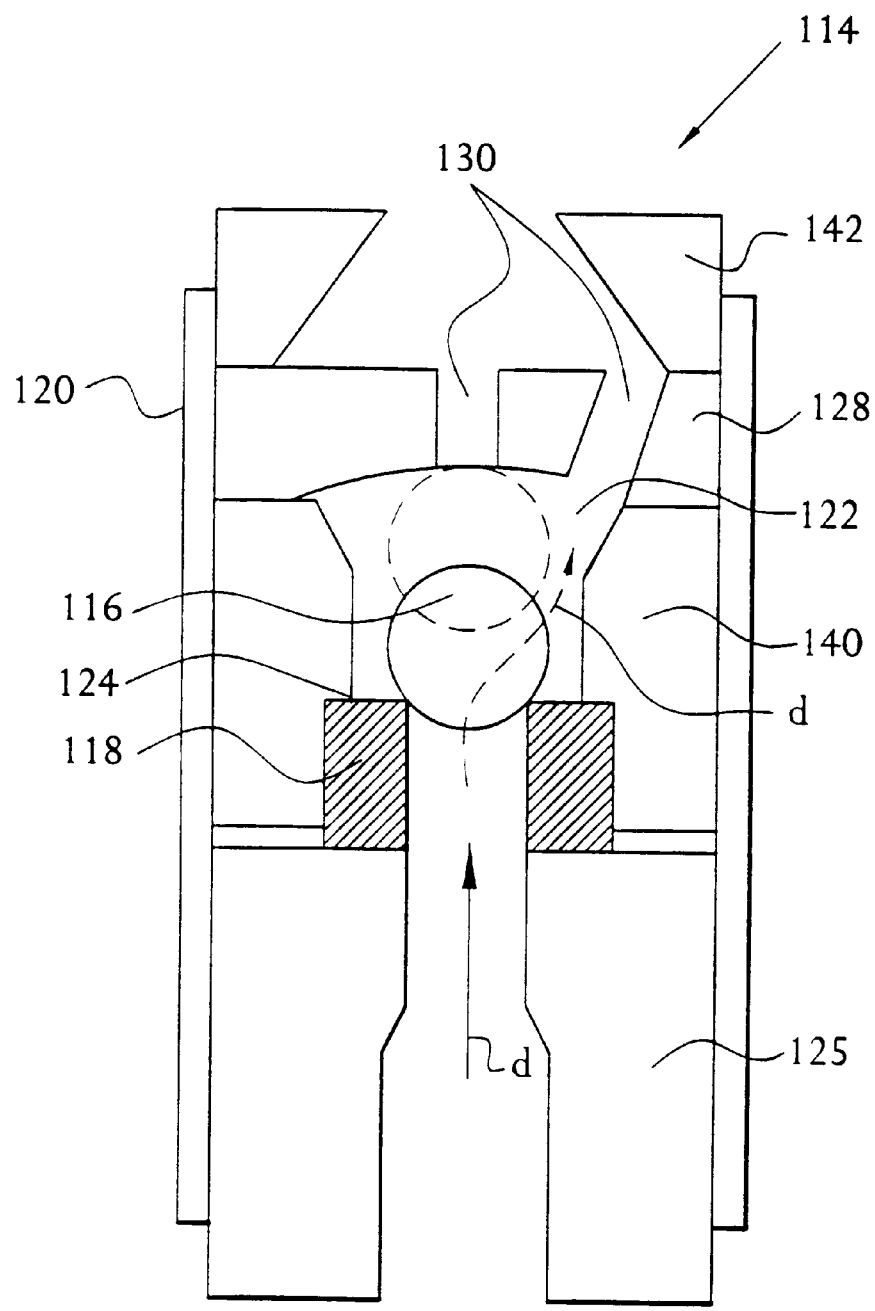
FIG. 7 is an isolated partially sectional front sectional view of a valve in accordance with the side arm reservoir of FIG. 6.

The high-pressure check valve 114 in the present embodiment is illustrated in the isolated sectional perspective view of FIG. 7. Preferably, the ball 116 and seat 118 are fabricated from very hard materials, because even moderately hard materials can tend to distort when driven against the valve seat at high pressures. This distortion can cause the ball 116 to "stick" in the seat 118 and seriously compromise valve function. Appropriately hard materials for high-pressure applications include industrial-grade ceramics such as ruby, sapphire and zirconia.

Because of the complex and precise spatial relationships required for proper functioning of the ceramic parts in the high-pressure valve 114, the most convenient form of the high-pressure valve is that of a "cartridge", which is essentially a sleeve 120, preferably of metal, in which all of the valve components are arranged in sequence axially, leaving sealing surfaces at the two ends. In this way, the valve can be conveniently inserted into the body of the pump and secured with a threaded fitting. Reversing this process enables the valve to be conveniently removed for repair or replacement.

Figure 8A:
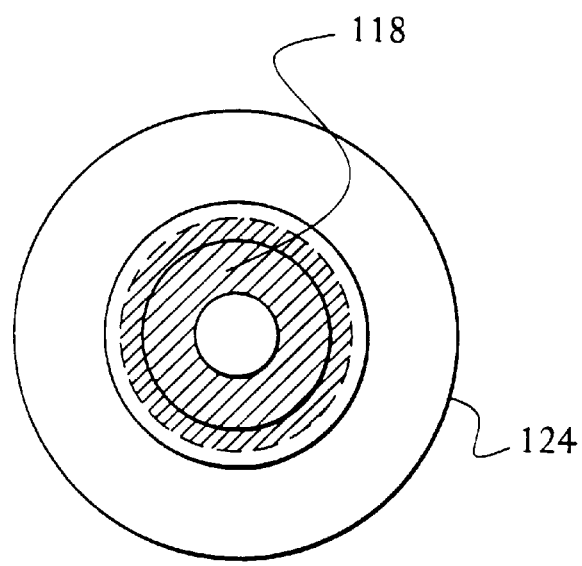
FIG. 8a is an isolated top plan view of a valve seat of FIG. 7.
Figure 8B:
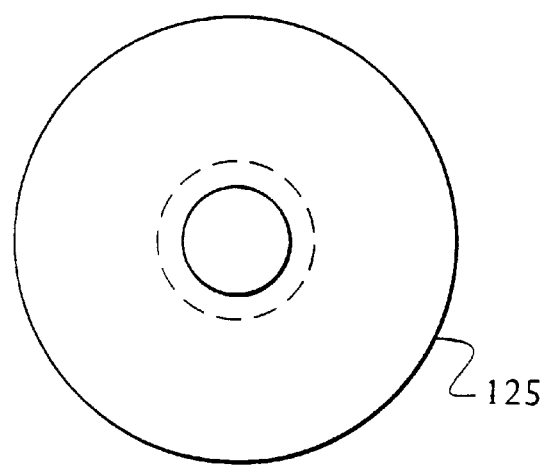
FIG. 8b is an isolated top plan view of a valve seat retainer of FIG. 7.
Figure 8C:
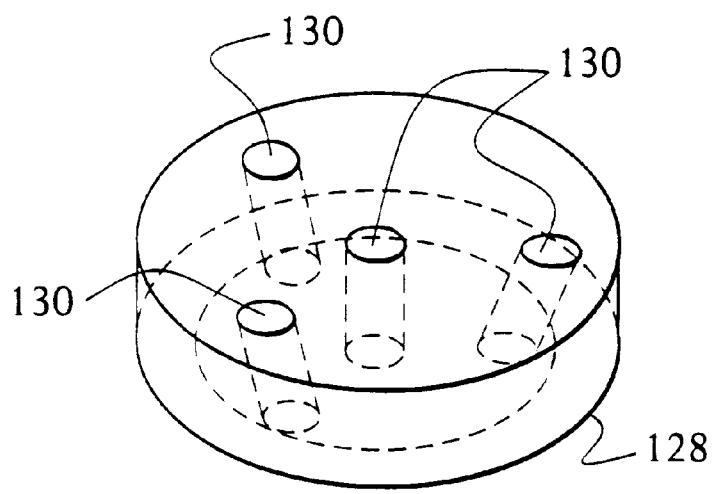
FIG. 8c is an isolated perspective view of a ball cage top of FIG. 7.
Figure 8D:
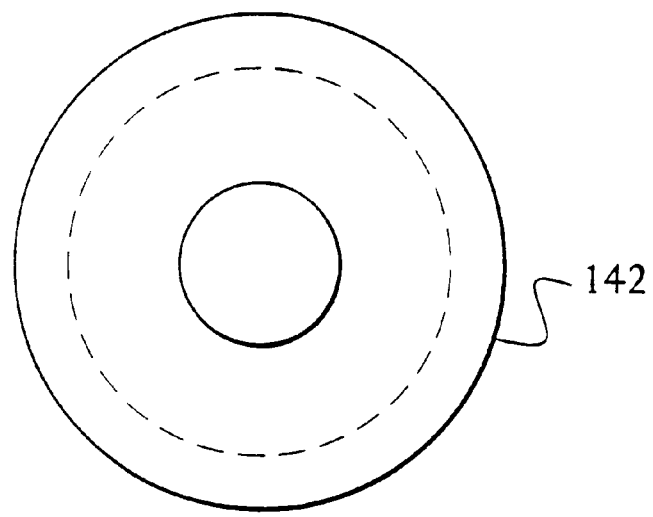
FIG. 8d is an isolated top plan view of a ball cage top retainer of FIG. 7.

To achieve a miniature valve 114 with high flow rates, the present embodiment uses the smallest readily-available ruby ball 116 (1/16" diameter) and sapphire seat 118 (0.0925" diameter), such as are available from Imetra, Inc. of Elmsford, N.Y. or Sapphire Engineering Inc. of Pocasset, Mass. The ball 116 is encaged in a cylindrical space 122 defined by the internal wall of the body 140. The space 122 is of such diameter (preferably 0.078" in the present embodiment) that material can freely flow around the ball 116 when the valve 114 is opened. The sleeve 120 also carries attached with the seat 118 a seat gland 124 and seat retainer 125, which are illustrated in detail in the isolated top plan views of FIGS. 8*a* and 8*b*, so that the seat 118 forms the bottom of the ball cage. A ball cage top 128 shown in detail in the perspective view of FIG. 8*c* preferably contains four small ports 130 (preferably 0.025" diameter in the present embodiment), comprising a single central straight port, and three peripheral ports, angled in the direction of the ball. The ball cage top 128 also preferably includes a concave lower surface facing the ball 116. In addition, a ball cage top retainer 142 shown in detail in the top plan view of FIG. 8*d* secures the elements in position.

In operation, when flow is in the direction of the arrow "d" of FIG. 7 and the ball 116 starts to move away from the seat 118, the area available for liquid flow around the ball is less than that available for flow in front of the ball, so that the ball moves rapidly away from the seat 118 into the position shown in dotted lines, thus opening the valve 114. In addition, when the ball reaches the top of the ball cage, the central port 130 allows liquid which is ahead of the ball 116 to move out of the ball cage, which action prevents the build-up of a liquid "cushion" which can slow the valving action. In addition, the concave surface of the ball cage top 142 serves to center the ball 116 over the central port 130. When the ball 116 is at rest against the central port 130 shown in dotted lines, the valve 114 is fully open. Preferably, the annular space defined by the outer diameter of the ball 116 and the inner diameter of the body 140 has a crosssectional area which is similar to that of the inlet and outlet ports of the valve 114, so that flow through the valve 114 is unimpeded. When the flow is reversed, the angled peripheral ports 130 in the ball cage top 128 "point" at the ball and serve to center the ball 116 as it is driven against the seat 118, minimizing the time required for valve closing and again adding to the "crispness" of the valving action.

The seat gland 124 in the sleeve 120 is preferably of such a length that when the seat 118 is pressed into the gland 124, a few thousandths of an inch (0.003" in the present embodiment) of the seat 118 protrudes beyond the margin of the gland 124. When the cartridge is installed in the pump body, and all of the internal (non-sleeve) parts are axially compressed by the action of the threaded fitting, this arrangement ensures that the valve seat 118 is held securely in place. Furthermore, the materials for the internal components of the valve cartridge are chosen so as to ensure proper sealing both between the individual components and against the sealing surfaces of the pump body and threaded fitting when the system is pressurized.

Figure 9:
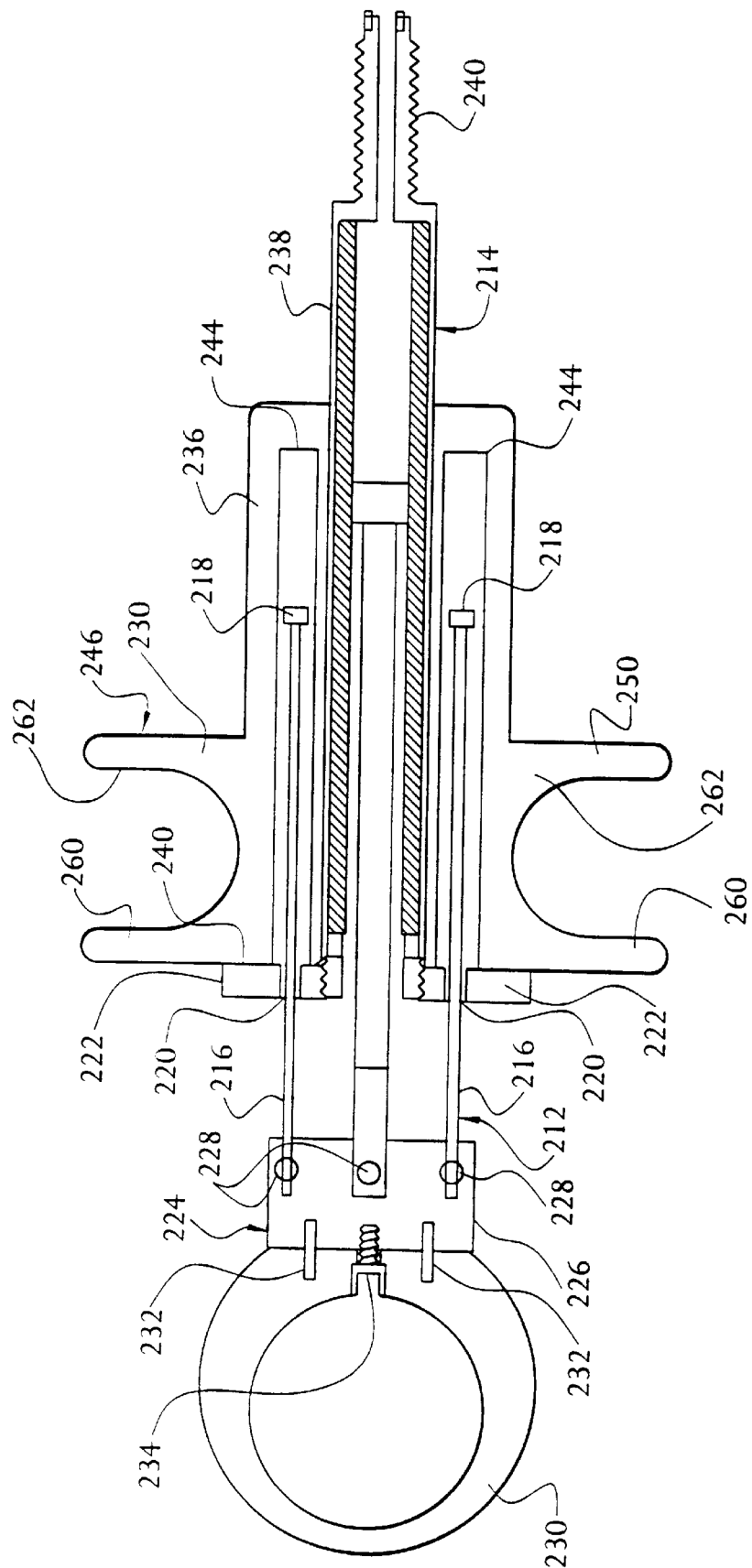
FIG. 9 is an enlarged, partially sectional front elevational view of another embodiment of a pressure generator of FIG. 1.

In FIG. 9 is a partially sectional front elevational view of still another embodiment of a pressure generator of FIG. 1. As will be described more fully hereinafter, the pressure generator shown in FIG. 9 comprises means for limiting plunger travel and actuation means for single hand operation. For purposes of this illustration, the limit means and actuation means are illustrated in connection with the syringe 30 illustrated in FIG. 4; however, it should be understood that the limit means and actuation means are equally applicable to the syringe 30 illustrated in FIG. 3. The limit means and actuation means features illustrated in the pressure generator of FIG. 9 are particularly advantageous in instances where the intrapulmonary aerosolizer 10 of the present invention is utilized in the "pump" mode for multiple doses, which requires that the plunger of the syringe work in a reciprocal motion. In particular, operation of the syringes illustrated in FIGS. 3 and 4 is a two-hand process, with one hand to hold the outer body member or barrel of the syringe and the other hand to work the plunger. Moreover, in the syringes illustrated in FIGS. 3 and 4, since the plunger tip is not visible through the stainless steel jacket, it may be possible to pull the plunger completely out of the barrel at the end of the retraction stroke, thus introducing air into the system and increasing the probability of contamination when the plunger is re-inserted into the barrel. The limit means and actuation means features illustrated in FIG. 9 will be described in more detail below. As should be understood, while both the limit means and actuation means features are illustrated in the syringe shown in FIG. 9, this is not required and each of these features may be separately provided where desired.

As illustrated in FIG. 9, the limit means preferably comprises retaining means 212 provided on the plunger (piston) which engages a portion of the syringe body 214 when the plunger is moved to its retracted position. In the present preferred embodiment, the limit means 212 comprises at least one and preferably two elongated rods 216 (preferably 0.0625" diameter) having slightly enlarged tips or bosses 218 (preferably 0.083" diameter) at the ends closest to the plunger tip, which are sized so as to be larger in diameter than the openings through clearance holes 220 (preferably 0.064" diameter) provided extending through the two flanges 222. In this embodiment, the ends of the rods 216 opposite the tip 218, as well as the end of the plunger opposite the plunger tip, are each preferably attached to a reciprocating body 224, such as by screws in the present embodiment. In a preferred embodiment illustrated in FIG. 9, the reciprocating body 224 comprises a block 226 substantially rectangular in this embodiment in which the rods 216 and plunger are attached by small set screws 228. In the present embodiment, the reciprocating body 224 further includes a thumb support 230 substantially ring-shaped in the present embodiment attached to the block 226 by alignment pins 232, which are received into both the block 226 and thumb support 230, and a screw 234 extending through the thumb support 230 and received into the block 226. As will be described in more detail below, the specific configuration of the reciprocating body 224 illustrated in the present embodiment is related to the actuation means feature of the present invention.

The pressure generator illustrated in FIG. 9 also includes a sleeve 236 having a substantially cylindrical aperture extending therethrough along its longitudinal axis for being inserted onto and around the outer body member 238 of the barrel of the syringe. In the present embodiment, the sleeve 236 is mounted in a position illustrated in FIG. 9 by being inserted over the threaded nose 240 and being press fit onto the outer body 238 of the syringe barrel, with the upper end 240 of the sleeve 236 coming into engagement with the flanges 222. In the present embodiment, the sleeve 236 also includes two opposing channels 244 within its upper end 240, aligned with the openings 220 in the flange 222, into which the rods 216 are received, which operates to house the rods 216 for added protection. Moreover, in the present embodiment, the sleeve 236 further includes a finger support 246, the purpose of which will be described in the following paragraph.

In accordance with the present embodiment, the actuation means are provided by the combination of the reciprocating body 224 and finger support 246. The finger support 246 in the present embodiment comprises opposing, generally square shaped members 250, each having substantially U-shaped cavities formed therein so as to be grasped with two fingers for operation. In another embodiment, the members 250 may each be formed as a ring having a central circular cavity extending therethrough into which each finger can be received. Furthermore, as discussed above, the reciprocating body 224 in the present embodiment includes an annular or ring-shaped thumb support 230, although, as should be understood, the support 230 can also be provided in other configurations as well. In operation, the syringe illustrated in FIG. 9 may be grasped with two fingers and the thumb of one hand via the finger support 246 and thumb support 230 and accordingly easily worked in a reciprocal motion. In the retraction mode, when pulling back with the thumb, upper legs 260 of the finger support 246 provide resistance. Similarly, in the contraction mode, when pushing inward with the thumb, lower legs 262 of the finger support 246 provide resistance. As indicated above, the interaction between the rods 216 and clearance holes 220 within the flanges 222 operate to prevent the plunger from pulling out of the barrel as the plunger is worked in a reciprocal fashion.

In the present embodiment, the thumb support 230 and body 236 are each preferably made of plastic, which is advantageous for comfort and weight considerations. The block 226 and rods 216 are each preferably made of metal in the present embodiment. The remaining portions of the syringe illustrated under FIG. 9 are described earlier in connection with the syringes shown in FIGS. 3 and 4, and will not be described in detail herein for this reason.

It will be recognized by those skilled in the art that changes may be made in the above-described embodiments of the invention without departing from the broad inventive concepts thereof. For example, the aerosolizer can be inserted through a port in the wall of an endotracheal tube, where the endotracheal tube itself is being used with a ventilator, with the aerosolizer either being positioned radially or coaxially within the endotracheal tube and, in the latter case, with the aerosolizer tip being located proximate the first bifurcation or carina. It should be understood, therefore, that this invention is not limited to the particular embodiments disclosed, but it is intended to cover all modifications which are within the scope and spirit of the invention as defined by appended claims.

I claim:

1. An intrapulmonary aerosolizer sized for intratracheal insertion or for being received into an endotracheal tube or bronchoscope positioned within a trachea and adapted for spraying a liquid material therefrom in close proximity to a subject's lungs, said intrapulmonary aerosolizer comprising:

a generally elongate sleeve member defining a first end and a second end and having a substantially longitudinally extending opening therethrough defining an inner sleeve surface, said sleeve member being adapted for receiving said liquid material;

a generally elongate insert defining a first end and a second end received within at least a portion of said substantially longitudinally extending opening of said sleeve member, said insert having an outer surface including at least one substantially helical channel provided surrounding said outer surface extending from the first end to the second end in a direction of said opening of said sleeve member and adapted for passage of said liquid material received by said sleeve member;

insert captivation means between said inner sleeve surface and said insert for retaining said insert within said sleeve member;

a body defining a first end and a second end and having an opening therethrough extending between said first end and said second end, said body being received within at least a portion of said longitudinally extending opening of said sleeve member and positioned between said insert and said second end of said sleeve member; and body captivation means between said inner sleeve surface and said body for retaining said body within said sleeve member, whereby said liquid material is adapted to be sprayed from said opening in said body.

2. An intrapulmonary aerosolizer according to claim 1, wherein said body captivation means further includes a first boss extending from said inner sleeve surface in engagement with said body proximate said second end of said body.

3. An intrapulmonary aerosolizer according to claim 2, wherein said first boss comprises a rolled-over portion of the second end of said sleeve member.

4. An intrapulmonary aerosolizer according to claim 2, wherein said insert captivation means further comprises a second boss extending from said inner sleeve surface in engagement with said insert proximate said second end of said insert.

5. An intrapulmonary aerosolizer according to claim 1, further comprising coupling means for attaching said first end of said sleeve member with a pressure generator adapted for delivering said liquid.

6. An intrapulmonary aerosolizer according to claim 5, wherein said pressure generator comprises a dispenser comprising:

an inner body member defined by a first end, a second end, an outer surface and an opening extending through said inner body member between said first end and said second end;

a piston disposed within said opening through said inner body member and moveable between contracted and retracted positions; and at least one outer body member defined by a first end, a second end defining an inner surface, an outer surface and an opening extending through said outer body member between said first end and said second end, wherein said inner body member is received substantially within said opening through said at least one outer body member.

7. An intrapulmonary aerosolizer according to claim 6, wherein said at least one outer body member is comprised substantially of a first material and said inner body member is comprised substantially of a second material, wherein said first material generally has greater tensile strength than said second material.

8. An intrapulmonary aerosolizer according to claim 7, wherein said first material is metal and said second material is glass.

9. An intrapulmonary aerosolizer according to claim 6, wherein said at least one outer body member further comprises:

at least two opposing flanges attached proximate the front end and extending outwardly therefrom;

a generally elongate retaining member having an outer surface engaging said inner surface of said at least one body member and positioned proximate said first end of said at least one outer body member, said retaining member further having an opening therethrough extending in a longitudinal direction of said at least one outer body member for receiving said plunger; and a sealing member received within said opening of said outer body member positioned between said retaining member and said inner body member, said sealing member having an opening therethrough extending in a longitudinal direction of said at least one outer body member for receiving said plunger.

10. An intrapulmonary aerosolizer according to claim 9, further comprising a second outer body member defining a first end, a second end, an outer surface and an opening extending through said second outer body member between said first and second ends defining an inner surface, wherein said second outer body member is positioned between said at least one outer body member and said inner body member, with said second outer body member being positioned substantially within said opening within said at least one outer body member and said inner body member being positioned substantially within said second outer body member.

11. An intrapulmonary aerosolizer according to any one of claims 9 and 10, wherein said at least one body member further comprises an end wall positioned at said second end, said end wall including an aperture therethrough receiving a generally elongate syringe tip, said syringe tip having an opening therethrough adapted for delivery of said liquid material from said inner body member.

12. An intrapulmonary aerosolizer according to claim 11, wherein said syringe tip is attached to said end wall of said at least one outer body member.

13. An intrapulmonary aerosolizer according to claim 11 wherein said syringe tip is attached to said inner body member and extends through said aperture through said end wall of said at least one outer body member.

14. An intrapulmonary aerosolizer according to claim 11, wherein said syringe tip includes an opening within its distal end and a seal position within said opening.

15. An intrapulmonary aerosolizer according to claim 6, wherein said dispenser further comprises reservoir means retaining a quantity of liquid for delivering said liquid to said inner body member upon moving said plunger into said retracted position and terminating delivery of said liquid to said inner body member upon moving said plunger into said contracted position.

16. An intrapulmonary aerosolizer according to claim 15, wherein said reservoir means includes a valve assembly comprising a generally elongate sleeve having an opening therethrough for receiving a ball and a valve seat, wherein said valve seat is generally elongate and includes a valve seat opening therethrough, whereby said ball is positioned on said valve seat substantially covering said valve seat opening when said plunger is moved into its contracted position adapted for blocking delivery of said liquid from said reservoir means, and said ball is dislodged from said valve seat when said plunger is moved into its retracted position for delivering said liquid from said reservoir means through said valve seat opening and to said inner body member.

17. An intrapulmonary aerosolizer according to claim 16, wherein said valve assembly further comprises a ball cage top received substantially within said opening through said sleeve so that said ball is positioned between said ball cage top and said valve seat, wherein said ball cage top includes at least one aperture therethrough for passing liquid from said reservoir means when said plunger is moved to its retracted position, and for passing liquid from said inner body member when said plunger is moved to its contracted position, so that said ball is moved by said liquid from said inner body member to be positioned on said valve seat so as to substantially block said valve seat opening.

18. A system for spraying a liquid material comprising:
generating means for delivering a liquid material pressurized to a level exceeding approximately 700 psi; and
aerosolizer means having proximal and distal ends and being sized for intratracheal insertion and having means for creating an aerosol located at its distal end and receiving said pressurized liquid material from said generating means for spraying said liquid material.

19. A system according to claim 18, wherein said aerosolizer means comprises means for spraying said liquid material as an aerosol with a median mass diameter of about 12 $\mu$m.

20. A system according to claim 19, wherein said generating means delivers said liquid material pressurized to at least about 2000 psi.

21. A system according to claim 18, wherein said aerosolizer means comprises a generally elongate member sized for intratracheal insertion and with said generally elongate member being operatively coupled to said generating means.

22. A system according to claim 21, wherein said generally elongate member comprises a first end, a substantially longitudinally extending cavity in said first end terminating by a wall proximate a second end, and an opening through said wall, wherein said generating means is operatively coupled to said generally elongate member proximate said first end and said liquid material is sprayed from said opening in said wall.

23. A system according to claim 22, wherein said generally elongate member further comprises an insert in said substantially longitudinally extending cavity.

24. A method for spraying a liquid material in close proximity to the lungs comprising the steps of:
providing an aerosolizer comprising:
a generally elongate sleeve member defining a first end and a second end and having a substantially longitudinally extending opening therethrough defining an inner sleeve surface, said sleeve member being adapted for receiving said liquid material;
a generally elongate insert defining a first end and a second end received within at least portion of said longitudinally extending opening of said sleeve member, said insert having an outer surface including at least one substantially helical channel provided surrounding said outer surface extending from the first end to the second end in a direction of said opening of said sleeve member and adapted for passage of said liquid material received by said sleeve member;
insert captivation means between said inner sleeve surface and said insert for retaining said insert within said sleeve member;
a body defining a first end and a second end and having an opening therethrough extending between said first end and said second end, said body being received within at least a portion of said longitudinally extending opening of said sleeve member and positioned between said insert and said second end of said sleeve member; and
body captivation means between said inner sleeve surface and said body for retaining said body within said sleeve member, whereby said liquid material is adapted to be sprayed from said opening in said body;
providing a dispenser comprising:
an inner body member defined by a first end, a second end, an outer surface and an opening extending through said inner body member between said first end and said second end;
a piston disposed within said opening through said inner body member and moveable between contracted and retracted positions; and
at least one outer body member defined by a first end, a second end, an outer surface and an opening extending through said outer body member between said first end and said second end defining an inner surface, wherein said inner body member is received substantially within said opening through said at least one outer body member;
providing coupling means for attaching said aerosolizer and said dispenser;
inserting said aerosolizer into a subject's trachea;
activating said dispenser for spraying said liquid material from said aerosolizer.

* * * * *